United States Patent [19]

Freeman

[11] Patent Number: 4,809,676
[45] Date of Patent: Mar. 7, 1989

[54] HEART ASSIST DEVICE AND METHOD OF IMPLANTING IT

[76] Inventor: Maynard L. Freeman, 5469 Ranier Dr., Lisle, Ill. 60532

[21] Appl. No.: 138,303

[22] Filed: Dec. 28, 1987

[51] Int. Cl.$^4$ .................. A61B 19/00; A61M 1/03; A61F 2/22
[52] U.S. Cl. .................... 600/16; 128/60; 128/DIG. 3; 623/3
[58] Field of Search .............. 128/1 D, 60, DIG. 3; 623/3, 1

[56] References Cited

U.S. PATENT DOCUMENTS

| | | | |
|---|---|---|---|
| 3,885,251 | 5/1975 | Pedroso | 128/1 D X |
| 4,014,318 | 3/1977 | Dockum et al. | 128/1 D |
| 4,448,190 | 5/1984 | Freeman | 128/60 |
| 4,583,523 | 4/1986 | Kleinke et al. | 128/1 D |
| 4,621,617 | 11/1986 | Sharma | 128/1 D |

Primary Examiner—Ronald L. Frinks
Attorney, Agent, or Firm—Bernard L. Kleinke

[57] ABSTRACT

An implantable heart assist device includes member to be surgically positioned about the aorta, and includes a series of electromagnetic segments connected electrically to a source of electricity implanted within or without the body. The electromagnetic segments are C-shaped, and are arranged in pairs. The segments of each pair are positioned opposite to one another in confronting relation surrounding the aorta, and the electrical source is used to energize the segments of each pair to cause the segments to be moved forceably toward one another electromagnetically. Thus, the aorta is squeezed between each pair of segments.

20 Claims, 1 Drawing Sheet

HEART ASSIST DEVICE AND METHOD OF IMPLANTING IT

DESCRIPTION

1. Technical Field

This invention relates in general to a new and improved implantable heart assist device and a method of implanting it. In particular, this invention relates to a device which helps propel blood through the aorta by implanting the device about aorta.

2. Background Art

Heart diseases, combined with circulatory diseases, pose a serious threat to an adult population. The sedative lifestyle, cholesterol-rich diet, obesity and other unhealthy habits contribute to the development of circulatory and heart diseases. The heart failure resulting from extended deficient heart function is, at best, a very debilitating condition, and at worst, is a terminal condition.

It is, therefore, of great importance to find and develop the heart assist devices which would provide a continuous, painless, comfortable and reliable support to a weakened or failing heart or circulatory system.

There have been many different types and kinds of medical devices and surgical procedures adapted for treating heart disease. For example, the artificial heart devices consisting of mechanical pumps have been implanted surgically to replace the failing heart in the circulatory system. Such pumps are typically actuated and controlled by an external, large base unit connected with the implanted pump through an opening in the chest wall of the patient. This kind of device greatly restricts movement and the activity of the patient, since the patient must, at all times, either be connected to the large, heavy life-supporting base unit, or must carry such unit with him or her in order to maintain the proper operation of the implanted pump. Other problems connected with such artificial heart devices have also been observed. There have been problems of immunologic or other rejection of the pump by the body. Also, since blood comes into contact with the pump, the fragile blood cells can become mechanically injured and hemolyzed as a result of the pumping action. Moreover, the connection for driving the heart pump entering the chest cavity, over a substantial period of time, can be a vehicle for transmitting infection to the patient.

Intra-aortic balloon heart pumps have also been employed. For example, a device shown in U.S. Pat. No. 3,505,987, includes an inflatable balloon or the like device which is inserted into the aorta extending from the heart, and then alternatingly inflated and deflated in synchronization with the beating of the heart, for creating counterpulsation to assist the heart function. In this regard, the balloon, when inflated, propels blood distally within the aorta to help improve the circulation of the patient. Moreover, blood is also forced within the aorta toward the heart, and thus into the coronary arteries to help nourish and strengthen the heart muscle.

However, the balloon comes into direct contact with the blood flowing in the aorta, and can cause similar adverse effects to those previously described for artificial heart devices. Also, the balloon must be inflated by means of a tube which connects the balloon with the output of an air compressor, and thus the opening for tube entering the body, may be a means of entrance for infection or other injury.

Thus, while such an apparatus has been employed successfully for some applications, due to the adverse side effects and the tethering to the air compressor apparatus, it has not proven to be entirely acceptable for very long term use. Also, the opening in the body for admitting the air tube must be cleaned meticulously on preferably a daily basis to avoid infection. Furthermore, the pumping of air into the intra-aortic balloon is not an entirely safe condition, since a leakage of air from the balloon into the blood stream, can cause an air emboly, which is an extremely dangerous condition for the patient.

In an attempt to design a long term implantable heart assist device, and one which does not require air tubes, an experimental electrical device was developed and is disclosed in an article, entitled "The Experimental Use of the Diaphragm as an Auxiliary Myocardium", *Surgical Forum*, IX, 266-268 [1958]. The experimental device was adapted to function with the left hemidiaphragm, a portion of the human diaphragm. The diaphragm is a muscle normally used for contracting the lungs. In this case, hemidiaphragm is removed surgically from the patient and then wrapped and sutured in place around the aorta. The diaphragm muscle is then stimulated electrically by two wires extending through an opening in the chest cavity from the diaphragm muscle to a source of electricity, to cause the diaphragm muscle to contract. As a result, a counter pulsation is achieved, without any portion of the device coming into contact with the blood being pumped.

However, this procedure does not appear to be practical for long term use. Firstly, the diaphragm, a body organ, must be mutilated, and as a consequence, the breathing function is severely impaired. Secondly, for long term use of the diaphragm, the diaphragm muscle would have to be stimulated artificially repeated, and it is inconceivable that the displaced muscle could withstand such repeated stimulations without damage and destruction of the muscle function. Consequently, the muscle would fatigue and die of exhaustion, or its function would become severely impaired.

Thus, it would be highly desirable to have either an external device attached to the outside of the body of a totally implantable heart assist device, which would not come into direct contact with the blood, and which could be used continually for long periods of time. Such a device should be relatively simple in its operation so as to function properly for long periods of time to assist the heart function. Such a device should not require excessive amounts of energy to power.

The device which addresses these requirements, is a heart assist device which can cause counterpulsation. Counterpulsation is a means of assisting the failing heart by propulsing arterial blood from the aorta before the ventricular ejection and moving it to the periphery and to the coronaries during diastole. The principle of counterpulsation can be very advantageous to the failing or weakened heart. Counterpulsation is also the method to increase the blood supply and hence more oxygen is provided to the myocardium and also to the body.

Counterpulsation of the blood flow means that the alternate compressing and releasing of the aorta is accomplished in synchronism with the heart beat, such that the compression occurs during diastole and the release occurs during systole. During diastole, when the heart is at rest and blood pressure is low, the aorta is squeezed to propel blood both distally away from the heart to improve circulation, and proximally toward the heart and into the coronary arteries to help nourish and strengthen the heart muscle and to provide sufficient supply of oxygen.

The counterpulsation device can be in the form of a large member, which encases the patient from the ankles to the thighs and contains an inflatable bladder. A hydraulic pump coupled to the patient's ECG fills the bladder with water during diastole, thus augmenting diastolic pressure and empties during systole. For example, reference may be made to an article, entitled *Emergency Medicine,* Oct. 15, 163-168 [1980].

The counterpulsing member, as described above, is very useful in emergency cases where the patient is hospitalized and bed-ridded anyway. However, it becomes completely impractical to the ambulatory patient. In such a case, the counterpulsing unit, which is heavy and limits totally the patient's movement, is impractical. Also, long term encasement of one extremity, is very unhealthy. The patient who could otherwise move around, walk or exercise, would be permanently bound to the place where the hydraulic pump is located.

An implantable heart assist device positioned between the ribs of a person and extends from the rib cage to the aorta of the heart to be assisted, is described in U.S. Pat. No. 4,583,523. The elongated assembly of this heart assist device includes an aorta compressing device at the front end thereof, for engaging the aorta externally thereof. A mounting device at the rear end of the elongated assembly, supports the device from the ribs of the person. A motive device actuates the deactivates the compressing device alternatingly to help pump blood through the arota in a counterpulsation mode of operation.

Another device which is totally implantable and attachable to the left ventiriculum, has been disclosed in U.S. Pat. No. 4,304,225. The device shown in that patent is mounted to a rib of the patient and includes a device for compressing a lower portion of the heart to facilitate the functioning thereof. Another device, which is mounted to the spine of the patient for compressing the aorta mechanically and repeatedly to achieve counterpulsation, has been disclosed in U.S. Pat. No. 4,448,190.

While the foregoing mentioned devices are advantageous for many applications, it would be highly desirable to have an heart assist device, which could be quickly and totally implantable in a relatively convenient manner, to minimize, or at least greatly reduce trauma to the patient. Without adversely affecting the health of the patient receiving such device, it should be placed outside of the blood stream, most preferably surrounding the aorta, to avoid the direct contact of the blood with any foreign material or body, which could otherwise injure the blood cells. The placement of the device outside of the blood stream would also prevent the mechanical internal aortal or heart injury by devices implanted or introduced into the heart or the blood-vessel.

It would also be highly desirable to have a long term ambulatory device which would not need to be connected through the opening in the chest cavity to any energy source, such as a source of compressed air, or a hydraulic apparatus. Therefore, it would be preferable to have an electrical device with relatively small energy demands, so that such energy can be supplied from a small battery, either implanted in close proximity to the device or in the body at a place which is easily accessible for recharging or exchange, such, for example, as a subcutaneous implantation.

Since, under the normal arrangement, any of such devices must overcome the resistance of the heart muscle or the resistance of the aorta the amount of energy required is enormous, and thus the extremely large energy source is needed. Therefore, it would be desirable to have a device which could provide all the benefits of the above mentioned devices, i.e. continuous counterpulsation, without requiring an excessively large sized energy source.

DISCLOSURE OF INVENTION

Therefore, it is the principal object of the present invention to provide a new and improved heart assist device and a method of implanting it, to assist the functioning of the weakened and failing heart.

Briefly, the above and further objects of the present invention are realized by providing a fully implantable heart assist device, and a method of implanting it totally within the body of a person requiring such heart assist device. The device, based on the principle of counterpulsation, assists the heart to provide the sufficient supply of blood into coronary arteries. It is activated during diastole, when the heart is at rest, and is fully implantable. The device avoids any contact with blood or other violent invasions of the aorta or heart.

An implantable heart assist device includes member to be surgically positioned about the aorta, and includes a series of electromagnetic segments connected electrically to a source of electricity implanted within or without the body. The electromagnetic segments are C-shaped, and are arranged in pairs. The segments of each pair are positioned opposite to one another in confronting relation surrounding the aorta, and the electrical source is used to energize the segments of each pair to cause the segments to be moved forceably toward one another electromagnetically. Thus, the aorta is squeezed between each pair of segments.

The segments are molded in a resilient protective sleeve. Within the sleeve, a first group of C-shaped segments arranged in a side-by-side configuration faces the second group of C-shaped segments disposed in a confronting relationship relative to corresponding ones of the segment of the first group of segments to form a plurality of split annular rings for surrounding the aorta. The electrical source energizes each individual segment to enable the supply of current flow through the pairs of segments, to create a magnetic field between the opposed segments of each pair. The magnetic field attracts individual segments of the first group to individual segments of the second group. The magnetic attraction of the pairs together help propel blood through the aorta distally into the body and proximally into coronary arteries in a counterpulsation manner.

The electrical source is controlled by a sequencing device to energize magnetically the pairs of segments seriatim. The sequencing device synchronizes the activation of the heart assist device with the diastole of the heart.

BRIEF DESCRIPTION OF DRAWINGS

The above mentioned and other objects and features of this invention and the manner of attaining them will become apparent, and the invention itself will be best understood by reference to the following description of the embodiment of the invention in conjunction with the accompanying drawings, wherein.

BEST MODE FOR CARRYING OUT THE INVENTION

Figure 1:
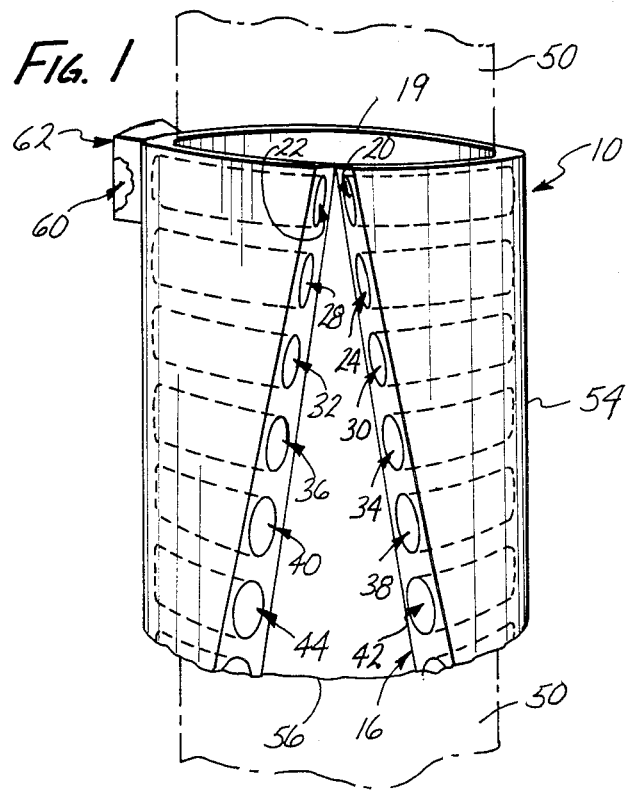
FIG. 1 is an elevational view of heart assist device which is constructed in accordance with the present invention.

Referring now to the drawings and more particularly to FIG. 1 thereof, there is shown a heart assist device 10, which is constructed in accordance with the present invention. The device 10 is implanted in the body surrounding an aorta 50 for helping propel the blood flow therethrough.

The device 10 generally comprises a sleeve device 19 surrounding the aorta 50, and an electrical energizing device 60 in a housing 62, which activates the sleeve device 19.

The heart assist device sleeve 19 is preferably implanted around the upper portion of the descending aorta; however, other portions of the aorta may also be used.

The housing 62 for electrical energizing device 60 is located at the external wall of the sleeve wrap device 19 but it may be located in other places inside or outside of the body. The electrical energizing device generally comprises a battery 80 and a sequencing circuit 91, as shown schematically in FIG. 2.

The mechanical and functional arrangement of the device 19 greatly reduces, the energy requirement for powering or driving it into operation, as compared to prior known devices. Thus, a smaller sized energizing device is required.

The heart distributes the blood the peripheral circulation by ejecting blood therefrom during the systole, and relaxes and fills with blood during the diastole of the body. During systole, the heart contracts and ejects blood under the high, systolic pressure. At the same time the aorta 50, an elastic blood-vessel, is distended and the blood flows forcefully under the systolic pressure. At this point any attempt to compress the aorta would otherwise require excessive amounts of energy in order to overcome the systolic pressure within the aorta. Hence, the energy supply would otherwise be of an excessively large size.

During the diastole, the heart relaxes and does not eject any blood, and thus the blood pressure in the aorta decreases. At that time, the aorta is being emptied of the blood, the pressure is much lower and the aorta is in a much more relaxed state.

During the diastole, the amount of blood in the arota is smaller, the resistance to any compressing or squeezing of aorta is much smaller and much less energy is required for compressing it. Nevertheless, the demand for energy even during the diastole is considerable, and to provide such amount of energy would still require an excessively large energy source.

Since the device 10 is operative only during the low pressure cycle of the heart function, there are smaller energy demands for activating it, as compared to conventional left ventricle assist devices, which function during the high pressure cycle of the heart. Thus, the device 10 does not require large, bulky power sources (not shown), and is totally implantable.

Additionally, according to the present invention, the construction and arrangement of the sleeve device 19 greatly facilitates the compression of the aorta, during diastole. The device 19 minimizes, or at least greatly reduces, the amount of electrical energy required to activate it in opposition to the aorta being squeezed by it.

Figure 2:
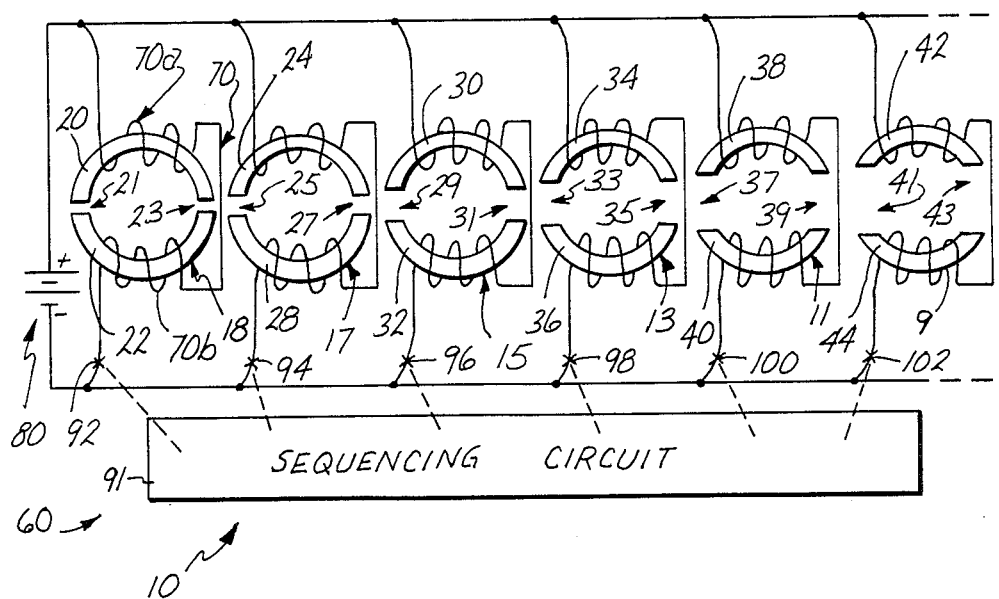
FIG. 2 is the schematic circuit diagram of the device of FIG. 1.

Referring now to FIGS. 1 and 2, the elimination of the high energy requirement is solved by the sequential arrangement of the sets of C-shaped segments 20, 22, 24, 28, 30, 32, 34, 36, 38, 40, 42 and 44. These segments are divided into the first group of segments 20, 24, 30, 34, 38 and 42, and into the second group of segments 22, 28, 34, 36, 40 and 44. All the segments are composed of metal material and are embedded in a resilient sleeve body 54, which is composed of any suitable thermoplastic material not rejectable by the body, such material as, a medical grade silicone rubber.

Pairs of confronting C-shaped segments 20 and 22, 24 and 28, 30 and 32, 34 and 36, 38 and 40 and 42 and 44 are arranged as a split ring configuration in a confronting relationship, with pair of narrow gaps 21 and 23, 25 and 27, 29 and 31, 33 and 35, 37 and 39, 41 and 43 relative to each other. Thus, for example, the segment 20 is disposed in a face-to-face confronting relationship relative to the segment 22 to form split rings generally indicated at 9, 11, 13, 15, 17 and 18, embedded within the body 54 (FIG. 1). All segments of the first group and all segments of the second group form a plurality of split rings for surrounding the aorta.

The pairs of gaps in the split rings 9, 11, 13, 15, 17 and 18, are progressively larger in size, starting with the gaps 21 and 23 between the segments 20 and 22. The segments all have the same shape. The sizes of the segments are progressively smaller, with each successive split ring pair, so that segments 20 and 22 are the largest in size, and the segments 42 and 44 are the smallest. The sizes of the gaps are increasingly larger starting with the gaps 21 and 23, which are the smallest in size, the segments 20 and 22 being the most closely spaced of the pairs at one end of the sleeve device 19. The split rings with gaps are arranged in such a manner that the ring segments with the narrowest gaps 21 and 23 is disposed at one end of the sleeve device, and is the pair which move toward one another when the device 10 is energized.

There are six pairs of segments shown in FIGS. 1 and 2. However, it is to be understood that the number of pairs of segments may be smaller or larger depending on the length of the aorta to be compressed to propel a sufficient quantity of blood through the aorta.

Considering now the construction of the sleeve device 19 in greater detail with reference to FIG. 1, the pairs of segments are arranged in an axially spaced apart manner along the axis of the body 54. The plane of each pair of segments is disposed transversely to the axis of the body 54, and the planes of the segment pairs are arranged parallel to one another.

The pair of segments 20 and 22 with the smallest gaps therebetween, are the first to move toward one another, and the remaining pairs of segments move individually and segmentally during successive intervals of time. Therefore, the device 10 compresses the aorta 50 in a progressive manner, and then releases it when the device 10 is de-energized. In this regard, when the magnetic field established in the segments terminates, the resiliency of the body 54 causes the segments to return to their positions as indicated in FIG. 1. Thus, the magnetic fields are established repeatedly within the segments, and terminated repeatedly to cause the sleeve to compress the release the aorta alternatingly.

When the magnetic field is established within a pair of segments, they move toward one another to shorten their gaps, against the force of the resilient body 54 and the blood filled aorta 50. When the segments 20 and 22 are energized, they are so closely spaced that they move readily toward and into contact with one another. In so doing, the end of the body 54 surrounding the segments 20 and 22 become slightly smaller in its inside diameter, and thus the next adjacent segments 24 and 28 are moved forcefully and mechanically by the body 54, as a result, the gaps 25 and 27 between the segments 24 and 28 are shortened by the closing of the adjacent segments 20 and 22.

Therefore, when the segments 24 and 28 are activated by establishing a magnetic field therein, the gaps 25 and 27 are sufficiently close together that the magnetic field can cause the segments 24 and 28 to move under the force of the magnetic field into engagement with one another.

In so doing, the adjacent gaps 29 and 31 of the segments 30 and 32 are shortened by the body 54. This action is repeated successively and progressively, until all of the segment pairs are closed.

Therefore, in accordance with the present invention, the arrangement of the segment pairs with the resilient body 54, helps narrow the gaps mechanically, so that a weaker magnetic field is required, and thus a smaller battery is needed.

The sleeve device 19, in its unstressed condition as shown in FIG. 1, has a V-shaped axial opening or split 16. Thus, the housing 54 surrounds and embeds all of the segments, but is opened at 16. In this manner, the sleeve device 19 can be slipped around the aorta 50.

The sleeve body 54 of the sleeve device 19 is composed of resilient, pliable material to assist in the mechanical closing of the segment gaps as they are activated electromagnetically. Also, due to the resiliency of the body 54, when the magnetic fields terminate, the segments move apart.

In order to protect the aorta from the repeated compression by the sleeve device 19, the aorta can be wrapped with a protective covering or bandage (not shown). Also, a protective sleeve (not shown) can be positioned about the aorta under the sleeve 19, by means of an internal hour-glass configuration to distribute the compressive forces applied thereby, as disclosed in the foregoing patents. The sleeve device 19 can have an internal smoothly contoured internal configuration molded into the body 54.

Referring now in greater detail to FIG. 2, there can be seen a schematic circuit diagram of the magnetic control of the rings 18, 17, 15, 13, 11 and 9. The battery 80 is connected by winding 70 with the ring 18 through series connected winding portions 70A and 70B. The winding portion 70A is wrapped about the segment 20 of ring 18. Winding portion 70B is wrapped about segment 22 of ring 18. Rings 9, 13, 15 and 17 have similar electrical windings as that described for the ring 18.

The winding portion 70B connected to the battery 80 is interrupted by a normally-opened switch 92. When the switch 92 is closed it connects the battery 80 across the winding 70 to energize electromagnetically the segments 20 and 22 to cause them to move together. For this purpose, a magnetic field is established across the gaps 21 and 23.

Switch 92 and similar switches 94, 96, 98, 100 and 102 are controlled via a suitable sequencing circuit 91, which may be disposed either on the outside of the sleeve device or outside of the body. The sequencing circuit 91 can be connected in close proximity to the winding within the housing 62 as shown in FIG. 1, or it can be placed either subcutaneously or at the outside of the body for controlling the operation of the device 10 remotely. The sequencing circuit 91 selectively and sequentially closes the switches starting with switch 92, and following with switches 94, 96, 98, 100 and 102 in that sequence. The switches are actuated magnetically by the sequencing circuit 91, and released thereafter, so that the operation can be repeated alternatingly. Attached to the sequencing circuit is a sensor 91A for synchronization of the switches with the heart beat of the patient. In other words, the opening of the switches is synchronized with the diastole. If the pulse rate increases, the rate of switch closure and opening also increases. If the pulse rate decreases, the rate of closing and opening of each switch also decreases.

The battery 80 serves an electromagnetic energy source. The battery may be located in the housing 62, or it may be placed elsewhere in the body, such as subcutaneously and connected with suitable conductors to the segments.

Returning now to the operation of the device 10, the sleeve device 19 is implanted about the aorta surgically. In order to implant the device 10 in a fast and efficient manner, a thoracotomy is performed, either employing an anterior or a posterior approach. In both procedures, an incision may be made between adjacent ribs. Thereafter, by working through the incisional opening, the aorta is wrapped with a bandage (not shown) of suitable material which protects the aorta against mechanical damage by continuous and long-term use of the device 10. The protective bandage is at least as long or longer axially than the sleeve device 19. The sleeve device 19 is then sized for placement and then implanted around it. The sleeve device 19 has an opening 16 in the body 54. The body 54 is wrapped around the protective bandage and may be affixed to it. The sequencing circuit 91 is then placed either inside the body, or outside thereof for remote control of the sleeve device 19.

When the sleeve device is in place, including all connections with electric energizing source, it can commence functioning.

During the systole of the body, the switch 92 is closed and the current establishing a magnetic field flows from the battery 80 through the winding 70 to establish magnetic fields in the segments 20 and 22. These segments are thus magnetically energized and move together to close gaps 21 and 23. Since the gaps 21 and 23 are relatively small in size, the amount of energy required is not very large. When closed, the segments 20 and 22 form the closed ring 19 which help propel blood through the aorta, both distally and proximally through the coronary arteries (not shown).

Subsequently, the sequencing circuit then closes switch 94 and the magnetic field develops the adjacent segments 24 and 28 to close the gaps 25 and 27. In so doing, the portion of the body 54 moves with the segments 24 and 28, and thus the adjacent portion of the body 54 moves the adjacent segments 30 and 32 toward one another.

The ring 17 then closes, although the gaps 25 and 27 between the segments 24 and 28 are normally relatively larger, due the body 54. The energy requirement for so doing will be also smaller. The closing of the ring 17 further helps propel the blood through the aorta distally and proximally, and creates the desired counter pulsation. Subsequently, the switch 96 closes to establish the electromagnetic field through the segments 30 and 32 to close the gaps 29 and 31. Closing of the gaps further propels the blood in both directions as previously described. Thereafter, under the control of the sequencing circuit 91, all of the rings close in sequence during diastole, thereby assisting in the desired blood flow through the aorta.

During systole, all of the switches are opened, and the electromagnetic circuit is broken, permitting the segments to return under the mechanical force of the sleeve 19, to their normal opened position with gaps opened.

Repeatedly, during the diastole of the person, the entire process recurs, i.e., closing of switches, developing magnetic fields, moving segments together, closing gaps, propelling the blood through the aorta distally and back to the coronary arteries. During the systole, the switches open, the electromagnetic field is broken, the segments return to their starting position, the gaps are opened, and so forth. In the succeeding steps, the squeezing of the aorta is preconditioned by sequencing.

During the activation of the device 10, the segments move closer and closer together to propel the blood more forcefully with each following pair of segments. However, for safety reasons, the segments never quite close the aorta, to cut-off the blood flow entirely through the aorta. In this regard, in case of inadvertent malfunction, the closing segments could not completely cut-off the blood flow through the aorta.

The number of rings is such that it allows the device 10 to help propel sufficient quantities of blood to resume blood flow to as close to a normal condition as possible.

Thus, an important advantage of the present invention is that there are separate segment rings which close progressively and successively. Because of the sequencing circuit, the segment are energized seriatim. Since the segments are controlled electrically, they may be controlled remotely by wireless connections (not shown), and synchronized with the heart beat.

While a particular embodiment of the present invention have been disclosed, it is to be understood that various different modifications are possible and are contemplated within the true spirit and scope of the appended claims. There is no intention, therefore, of limitations to the exact abstract or disclosure herein presented.

What is claimed is:

1. A heart assist device for helping propel blood through the aorta, comprising:
   a first group of generally C-shaped segments composed of magnetic material; said segments being arranged in a side-by-side configuration;
   a second group of C-shaped segments disposed in a confronting relationship relative to corresponding ones of the segments of said first group of segments to form a plurality of split annular rings for surrounding the aorta;
   electrical means for supplying current flow through pairs of said segments to establish magnetic fields therein to attract magnetically individual ones of the segments of the second group; and
   sequencing means for controlling said electrical means to cause it to energize magnetically the pairs of segments seriatim.

2. The device of claim 1, wherein the device is sized for placement around and along the aorta.

3. The device of claim 2, wherein the device is sized for placement around and along the descending portion of the aorta.

4. The device of claim 3 wherein there are four or more segments.

5. The device of claim 4 wherein there are six segments

6. The device of claim 4 wherein the pairs of segments in annular rings are arranged from largest to smallest in descending manner and the gaps are arranged from smallest to largest in descending manner.

7. The device of claim 6 wherein the segments are embedded in a resilient body.

8. The device of claim 7, wherein said body is composed of medical grade silicone rubber.

9. The device of claim 8 wherein the electrical means for supplying current flow through segment are arranged sequentially.

10. The device of claim 9 wherein the sequential arrangement is such as to allow the development of magnetic field seriatim across the gaps between the segments in such a manner that the magnetic field develops first across the smallest gaps between the largest segment and continues to develop sequentially and progressively across the larger gaps and smaller segments.

11. The device of claim 10 wherein the sequential control is achieved by sequencing means.

12. The device of claim 11 wherein the sequencing means includes a sensor.

13. The device of claim 1 wherein said electrical means includes windings wrapped about said segments.

14. The device of claim 13 wherein said electrical means includes switches controlled by said sequencing means.

15. The device of claim 14 wherein the electrical energizing means is a battery.

16. The device of claim 15, wherein the battery is adapted to be located subcutaneously.

17. The device of claim 15 wherein the battery is located externally.

18. A method of propelling blood bidirectionally through the aorta, comprising:
   repositioning a first group of generally C-shaped segments composed of magnetic material; said segments begin arranged in a side-by-side configuration;
   disposing a second group of C-shaped segments disposed in a confronting relationship relative to corresponding ones of the segments of said first group of segments to form a plurality of split annular rings for surrounding the aorta;
   using electrical means for supplying current flow through pairs of said segments to establish magnetic fields therein to attract magnetically individual ones of the segments of said first group to individual ones of the segments of the second group; and
   controlling said electrical means with sequencing means for controlling said electrical means to cause it to energize magnetically the pairs of segments.

19. The method of claim 18 wherein said controlling is seriatim.

20. The method of claim 19 wherein the developing of magnetic field is coincidental with the heart diastole.

* * * * *

UNITED STATES PATENT AND TRADEMARK OFFICE
CERTIFICATE OF CORRECTION

PATENT NO. : 4,809,676

DATED : March 7, 1989

INVENTOR(S) : Maynard L. Freeman

It is certified that error appears in the above-identified patent and that said Letters Patent is hereby corrected as shown below:

Column 3, line 31 after "actuates", delete "the" and substitute therefor "and".

Column 5, line 34 after "blood" please insert -- to --.

Column 9, line 64 after "the segments of" please insert -- said first group to individual ones of the segments of --.

Signed and Sealed this

Seventeenth Day of October, 1989

Attest:

DONALD J. QUIGG

Attesting Officer

Commissioner of Patents and Trademarks